(12) United States Patent
Singh

(10) Patent No.: US 6,599,237 B1
(45) Date of Patent: Jul. 29, 2003

(54) INSTRUMENT AND METHOD FOR FACILITATING ENDOSCOPIC EXAMINATION AND SURGICAL PROCEDURES

(76) Inventor: Errol O. Singh, 1988 Cambridge Blvd., Upper Arlington, OH (US) 43221

( * ) Notice: Subject to any disclaimer, the term of this patent is extended or adjusted under 35 U.S.C. 154(b) by 0 days.

(21) Appl. No.: 09/480,347

(22) Filed: Jan. 10, 2000

(51) Int. Cl.[7] .............................................. A61M 25/00
(52) U.S. Cl. ...................... 600/114; 600/115; 600/135; 604/164.05
(58) Field of Search ................................. 600/105, 114, 600/115, 116, 135; 604/164.05, 161, 164.03

(56) References Cited

U.S. PATENT DOCUMENTS

| | | |
|---|---|---|
| RE31,855 E | 3/1985 | Osborne |
| 4,581,025 A | 4/1986 | Timmermans |
| 4,768,858 A | 9/1988 | Hussein |
| 4,842,582 A | 6/1989 | Mahurkar |
| 4,893,623 A | 1/1990 | Rosenbluth |
| 5,002,558 A | 3/1991 | Klein et al. |
| 5,147,335 A | 9/1992 | Wright |
| 5,192,286 A | 3/1993 | Phan et al. |
| 5,209,725 A | 5/1993 | Roth |
| 5,249,585 A | 10/1993 | Turner et al. |
| 5,281,212 A | 1/1994 | Savage et al. |
| 5,290,294 A | 3/1994 | Cox et al. |
| 5,301,687 A | 4/1994 | Wong et al. |
| 5,304,214 A | 4/1994 | DeFord et al. |
| 5,312,399 A | 5/1994 | Hakky et al. |
| 5,366,456 A | 11/1994 | Rink et al. |
| 5,409,483 A | 4/1995 | Campbell et al. |
| 5,415,165 A | 5/1995 | Fiddian-Green |
| 5,417,653 A | 5/1995 | Sahota et al. |
| 5,454,807 A | 10/1995 | Lennox et al. |
| 5,480,417 A | 1/1996 | Hascoet et al. |
| 5,509,929 A | 4/1996 | Hascoet et al. |
| 5,549,601 A | 8/1996 | McIntyre et al. |
| 5,573,531 A | 11/1996 | Gregory |
| 5,586,982 A | 12/1996 | Abela |
| 5,593,713 A * | 1/1997 | De La Luz-Martinez et al. ...................... 219/771 |
| 5,628,770 A | 5/1997 | Thome et al. |
| 5,649,923 A | 7/1997 | Gregory et al. |
| 6,033,413 A * | 3/2000 | Mikus et al. .......... 604/102.01 |
| 6,086,528 A * | 7/2000 | Adair ...................... 600/104 |

OTHER PUBLICATIONS

Chiou et al., "Placement of Large Suprapubic Tube Using Peel–Away Introducer." *The Journal of Urology*, Apr. 1995, vol. 153, 1179–1181.

* cited by examiner

*Primary Examiner*—John Mulcahy
(74) *Attorney, Agent, or Firm*—James V. Harmon (57) ABSTRACT

A surgical instrument includes a working sheath and an obturator. A method is also described for facilitating endoscopic examination and surgical procedures using such an instrument. The sheath is an elongated self-supporting tube with a lumen of sufficient size to accommodate other surgical instruments. During use, the instrument is placed in the body percutaneously or through a body passage with the removable obturator located in the lumen to facilitate insertion of the sheath into the body. Once inserted, the obturator can be removed. The sheath is held in place by an inflatable bulb provided on the distal end of the sheath while the operation is being completed. A peripheral duct is also preferably provided for introducing anesthetic or lubricant during insertion. Any of various instruments selected by the surgeon, including instruments that are larger than the lumen of the sheath, can be inserted and removed by being passed into the body through the lumen of the sheath while the sheath remains in a substantially fixed position. The sheath thus acts as an artificial protective lining for the body opening through which it is passed, e.g., the urethra.

6 Claims, 5 Drawing Sheets

INSTRUMENT AND METHOD FOR FACILITATING ENDOSCOPIC EXAMINATION AND SURGICAL PROCEDURES

FIELD OF THE INVENTION

This invention relates to surgery and more particularly to a tubular working sheath and obturator and to a method for using the same.

BACKGROUND OF THE INVENTION

In several kinds of surgical operations, e.g., urological procedures, it is the current practice to insert and remove various instruments through the urethra several times during a single surgical operation. The repeated insertion and removal of instruments often requires a significant amount of force. This can of course traumatize the tissue. It is therefore a general object of the present invention to eliminate the need for inserting and removing a series of surgical instruments by passing them through an opening in the body in a manner that can cause discomfort or injure the tissue and in that way reduce the possibility of bleeding, trauma, inflammation, infection, false passage, and long-term complications such as scarring.

In addition, the manipulation of a surgical instrument or other object that is partially or completely inserted into the body can also result in damage to the surrounding tissue. A more specific object of the invention is to minimize the possibility of damaging the tissue through either the manipulation or the repeated insertion and removal of instruments that have to be used in succession to complete a surgical operation. For example, in many urologic procedures a cystoscope is inserted blindly or under direct vision for evaluation and diagnosis. The cystoscope is frequently removed and another instrument then inserted for lavage, cauterization, extraction, lavage or surgery. Not infrequently, a series of such instruments are inserted in succession. Finally, at the conclusion of the endoscopic or percutaneous procedure, it is frequently necessary to insert a catheter to divert urine or a drain. The insertion and removal of each of these other instruments increases the chances for traumatizing or injuring surrounding tissue or even creating a false passage and losing access. Moreover, each time a body orifice, i.e., oral cavity, urinary, gastrointestinal tract or other opening is manipulated, the potential for bacteremia is increased. In short, tissue trauma can result from retrograde or antegrade passage instrumentation or removal of foreign bodies. Moreover, many endoscopic, percutaneous or laparoscopic instruments have a relatively small diameter working channel which limits the size of biopsy specimens. The small size limits the removal of such specimens or foreign bodies by necessitating multiple insertions and withdrawals. This prolongs the operation and is an additional source of tissue trauma. Finally, when one instrument is removed and replaced by a second instrument, positioning the distal end of the second instrument is inexact because there is nothing present to locate the second instrument at a predetermined stop point with respect to the position taken by the previous instrument.

While it is known in the art to use a sheath to facilitate the insertion of a small catheter into the body, as described for example in U.S. Pat. Nos. 4,581,025 and RE31,855, no provision is made for accommodating a series of surgical instruments including endoscopes, cauteries, or instruments used in removing tissue for biopsy. Moreover, no provision is made for holding the patented sheath in place nor is there any provision for introducing anesthetic or medication. Accordingly, it is a more specific object of the invention to provide a method and surgical instrument that can be placed percutaneously or transurethrally for facilitating both endoscopic surgery or cystoscopic procedures so as to ease the successive placement, manipulation and removal of various surgical instruments including relatively bulky or rigid instruments such as endoscopes, cautery instruments, cold knife scalpel instruments, and biopsy instruments without increasing the likelihood of bleeding, trauma, inflammation and long-term complications. Another object of the invention is to provide such an instrument with a provision for holding itself securely in place during use while permitting introduction of fluids, e.g, for irrigating the tissue or for anesthesia, etc., and for accommodating instruments that are larger than the lumen of the working sheath. Yet another object of the invention is to provide a method for using such an instrument.

These and other more detailed and specific objects of the present invention will be better understood by reference to the following figures and detailed description which illustrate by way of example of but a few of the various forms of the invention within the scope of the appended claims.

SUMMARY OF THE INVENTION

Briefly, the invention is concerned with a surgical instrument, comprising, a working sheath and obturator as well as a method for facilitating endoscopic examination and surgical procedures using such an instrument. The sheath is an elongated self-supporting tube with a lumen of sufficient size to accommodate other surgical instruments. During use, the instrument is placed into the body percutaneously or through a body passage into a body cavity, e.g., endoscopically through the urethra, trachea, esophagus or rectum, or into the peritoneal cavity. A removable obturator is provided in the lumen to facilitate insertion of the sheath into the body. Once inserted, the obturator can be removed. Following this, the sheath is not moved while the operation is being performed. An inflatable balloon is preferably provided on the distal end of the sheath to hold it in place and thereby prevent retrograde movement. A peripheral duct or channel is also preferably provided for introducing lubricants during insertion or anesthetic during the procedure. While the working sheath remains in the body, any of various instruments selected by the surgeon, including instruments that are larger than the lumen of the sheath, can be inserted and removed by being passed into the body through the lumen of the sheath while the sheath remains in a substantially fixed position, i.e., stationary. The sheath thus acts as an artificial protective lining for the body opening through which it is passed, e.g., the urethra, gastrointestinal tract, bronchial tract, or percutaneous opening. The sheath can be used to introduce anesthetic and optionally lubricants to reduce discomfort or pain during insertion. In addition, the sheath can be used, if desired, to locate the distal end of any of a series of surgical instruments at a selected stop point with respect to the position taken by a preceding instrument. This feature may be very helpful with procedures under fluoroscopic (x-ray) guidance.

The invention thus provides a working sheath which can be thought of as a temporary and removable artificial tract or liner that is placed through an opening in the body of the patient at the beginning of a surgical procedure to facilitate endoscopic evaluation and treatment of the urinary tract or other body cavity for minimizing trauma and patient pain. During use, it allows multiple insertions and removals, i.e., the interchange of endoscopic instruments, catheters, drains, etc. At its proximal, i.e., outer end, the lumen of the sheath has an entry port for instruments with a removable cap that provides a nipple seal to preclude backflow of fluid from the body after the obturator has been removed. The instrument can be placed into the urethra blindly with an obturator in the lumen or under direct vision, i.e., with a fiber-optic scope extending through the sheath to act as an obturator. In other words, the obturator itself can comprise a fiber-optic bundle for illuminating and viewing a body cavity through the sheath, both during the insertion of the sheath and thereafter.

DETAILED DESCRIPTION OF THE INVENTION

As mentioned briefly above, the working sheath of the present invention can be thought of as a temporary and removable artificial tract device or liner that is placed percutaneously or transurethrally to facilitate endoscopic evaluation and/or treatment of the urinary tract and other body cavities by enabling other surgical instruments to be passed through it into the body so as to minimize tissue trauma, discomfort or pain. Typically the sheath is about 40 cm long and has a central lumen that is typically about 6 MM to 10 MM in diameter. An inflatable circumferentially extending balloon is provided at its distal end. At the proximal end of the sheath are two tubular extensions for introducing fluid through longitudinally extending peripheral ducts or channels to be described in detail below. One channel is used for expanding a balloon to retain the sheath in place in the body. The second channel is used for introducing an anesthetic, medication or lubricant. The sheath preferably has a smooth finish with a low coefficient of friction. Optionally, a low friction coating can be provided to facilitate placement of the sheath within the body. The sheath can be formed from any of various well-known commercially available polymeric materials and can be either a resilient material such as rubber or a stiffer material such as plastic, e.g., a polyolefin. Silicone or latex rubber, polypropylene or polyphylenene is preferred. When the sheath is formed from highly flexible material, a relatively stiff obturator is placed within the sheath to facilitate insertion of the sheath into the body. The sheath is inserted only once at the beginning of a procedure and therefore can be thought of as a single insertion instrument.

Refer now to the figures, and particularly to FIGS. 1–5.

As shown in the figures, the sheath, indicated generally by the numeral 10, has an elongated body portion 12 with a distal end 14 and an a proximal end 16. Inside the sheath 10 is a lumen or working channel 18 that extends the entire length of the sheath 10 and is provided with a distal opening 20 at one end and a proximal opening 22 at the opposite end. It will be noted that the distal end 14 of the sheath 10 adjacent the opening 20 is tapered at 21 so that its outer diameter is progressively reduced proceeding toward the opening 20. The sheath 10 can vary in length to suit the application to which it is applied, but in general it is typically from 30 cm to 50 cm in length and is preferably about 40 cm in length when it is to be used for gynecological procedures. It can be longer, say, 50 cm in length, when used in the male, for example in a transurethral resection of a bladder tumor. For transurethral use, the outside diameter is typically about 9 mm and the inside diameter about 5 mm. It should be understood that the dimensions presented herein are merely typical and can be varied to suit the circumstances in which the instrument is used.

At the distal end 14 of the sheath 10 is provided an inflatable circumferentially extending annular balloon 24 formed from a ring of resilient material such as synthetic rubber, latex rubber or the like, that extends around the sheath 10 adjacent the distal opening 20. It will be noted in FIG. 4 that the balloon 24 does not extend entirely around the sheath 10 but is provided with ends 24a and 24b that give the balloon 24 a C-shaped configuration (FIG. 4) for purposes to be described below. Inflation air or liquid is supplied to the balloon 24 when required through a tubular extension 26 at the proximal end 16 of the sheath 10. If the sheath 10 is formed from an elastomer such as rubber, the balloon 24 can be integral with the sheath. However, if the sheath 10 is formed from a firm plastic material such as polypropylene, the balloon 24 is formed from rubber that is bonded to the outside surface of the sheath 10, e.g. by means of a. suitable adhesive. The proximal extension 26 has a central passage 28 for inflation air or liquid which communicates with a longitudinally extending peripheral channel 29 that has a distal opening 31 communicating with the interior of the balloon 24. The free end of the tubular extension 26 is provided with an inflation port that preferably includes a Luer lock 30 through which inflation fluid (gas or liquid) can be introduced and retained until the Luer lock is opened.

The proximal end 16 of the sheath 10 has a second tubular inlet comprising an extension 32 with a central passage 34 that communicates through a longitudinally extending peripheral duct 36 with an opening 38 located a short distance, e.g. 1 or 2 cm, proximal of the balloon 24. The passage 34 terminates at its free end in an opening 40 that is sealed, e.g. by means of Luer lock 42. During use, an anesthetic, lubricant or other fluid can be introduced through the inlet 40 into the passage 34, the duct 36 and exits through opening 38 into the urethra, a portion of which is shown at 44 adjacent to the urinary bladder 46. The anesthetic or lubricant introduced in this way during placement in the urethra 44 will allow the sheath 10 to slide easily through the urethra 44 and will reduce patient discomfort. Endoscopic procedures thus can be performed with topical anesthesia supplied through the opening 38, with minimal sedation or light general anesthesia.

An advantageous feature of the invention is that the topical anesthetic or medication supplied through the opening 38 is retained between the tissue and the sheath 10, thus preventing flushing so as to provide longer retention and effectiveness. Although the initial discomfort or pain will usually require topical or general anesthesia at the time of initial placement, the pain will become attenuated as a result of the topical anesthetic retention made possible by supplying the anesthetic through the opening 38 as described. The instillation of the topical anesthetic can be administered intermittently as necessary through the delivery port 38 distal to the retention balloon 24. For example, lidocaine or other topical anesthetic solution or gel that is used for patient comfort can be diffused into the urethra lumen as the working sheath 10 is inserted. This holds or locks the medication between the urethral inner wall and the outer wall of the sheath 10 which will not absorb or allow the medication to flush or drop out, thus considerably concentrating and prolonging its effect. At the proximal end 16 of the sheath 10 is a circumferentially extending digital grasp ring or sleeve 48 which can, if desired, be provided with a non-slip knurled or other suitable high friction surface to make the grasp ring easy to hold onto as the sheath 10 is being manipulated. The ring 48 is preferably bonded to the sheath 10 by means of a suitable adhesive but, if desired, can be integral with the sheath 10. The tubular extension 32 can be used for any of a variety of purposes including, but not limited to, lavage, aspiration, irrigation, the introduction of medication such as an anesthetic, lubricant or antibiotic, or for other purposes. The extensions 26 and 32 are preferably about 120° apart when the sheath 10 is viewed from one end.

In the lumen 18 of the sheath 10 (FIGS. 1 and 2) is placed an elongated generally cylindrical obturator 50 having a parabolic insertion tip 52 at its distal end and. optionally an enlarged head 54 at its proximal end, which functions as a handle to enable the obturator 50 to be easily inserted and removed from the lumen 18 of the sheath 10. It can be seen that the tapered portion 21 of the sheath 10 and the parabolic insertion tip 52 of the obturator 50 form a smoothly contoured surface that facilitates introduction of the instrument into the body, for example during a transurethral insertion through the urethra 44 into the bladder 46.

Figure 1:
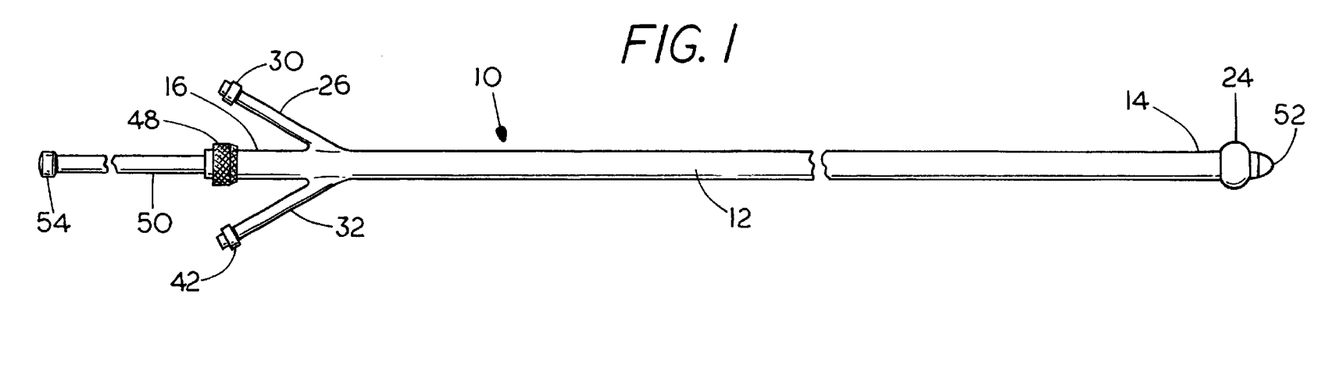
FIG. 1 is a plan view of an instrument in accordance with the invention.
Figure 2:
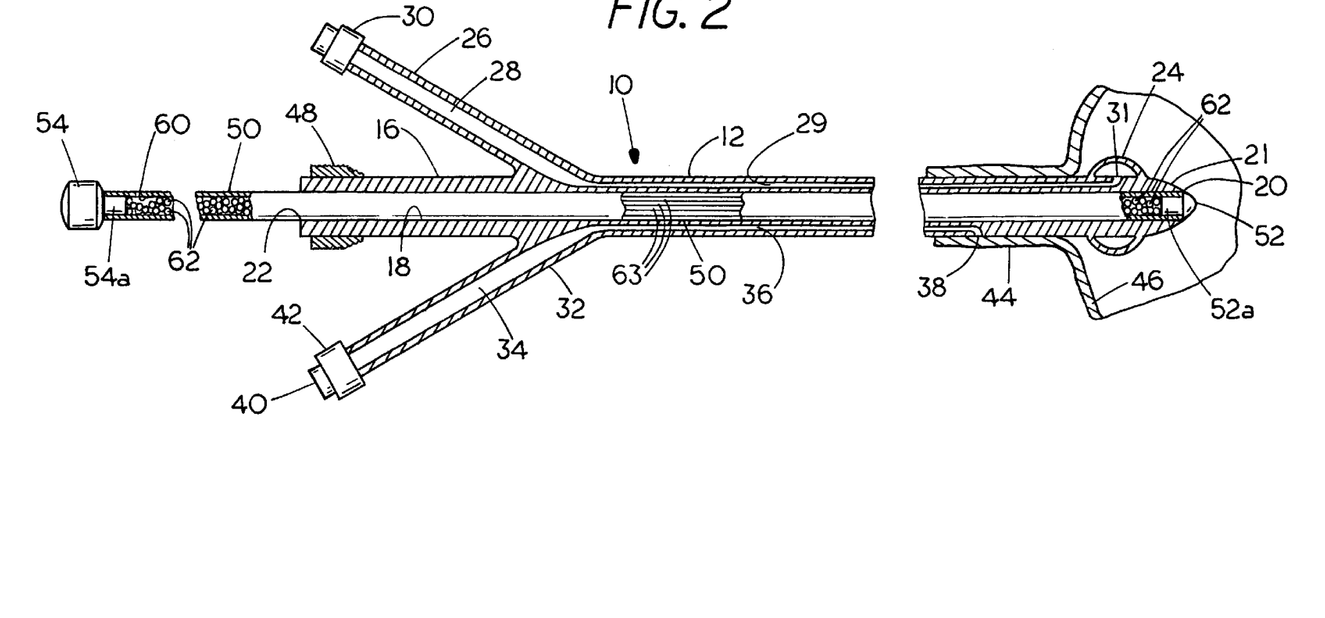
FIG. 2 is a longitudinal cross-sectional view of the instrument on a larger scale as it appears when inserted into a body cavity, in this case through the urethra into the bladder.
Figure 2A:
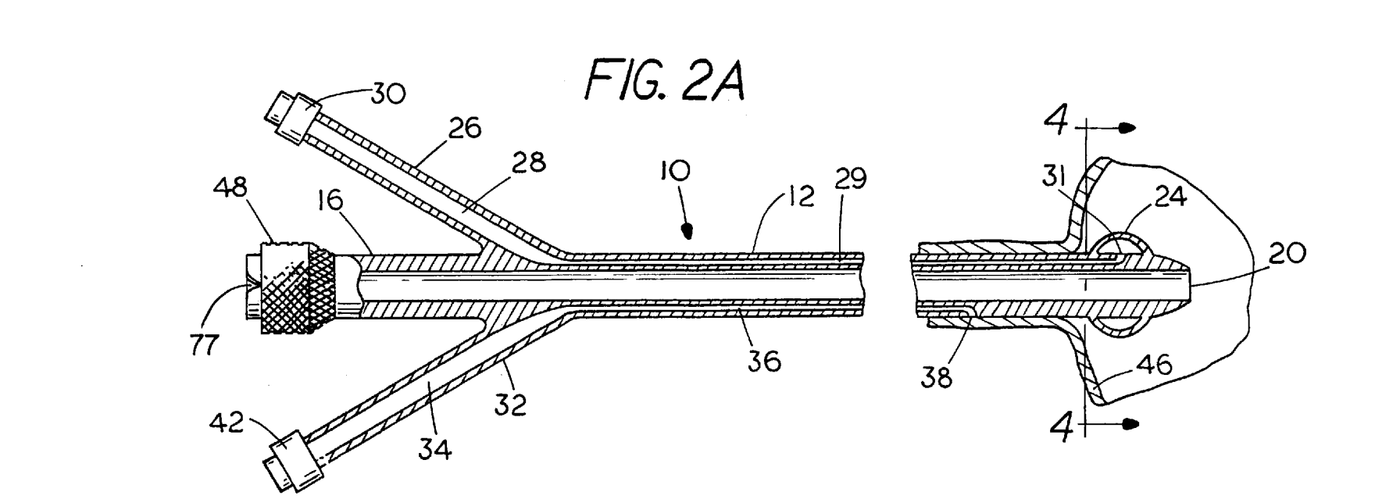
FIG. 2A is a view similar to FIG. 2 with the obturator removed.
Figure 3:
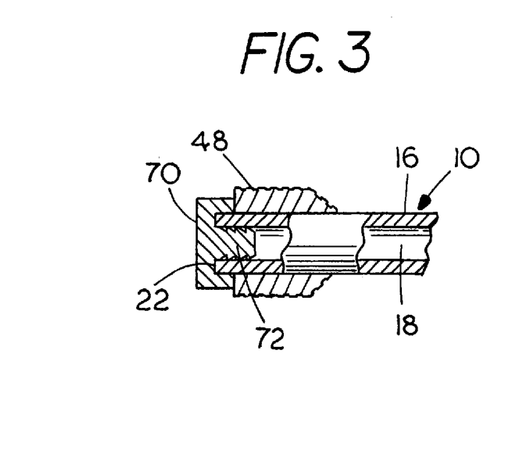
FIG. 3 is a partial vertical longitudinal sectional view of the proximal end of the instrument in a sealed condition.

Refer now to FIG. 2 which illustrates a preferred form of obturator 50 in accordance with the present invention. Although the obturator 50 can be solid, in one form it comprises a stiff-walled tube having an interior 60 that is filled with internal supporting elements such as plastic beads 62. The beads 62 will enable the obturator 50 to flex at right angles to its longitudinal axis but will reliably prevent the obturator 50, as well as the sheath 10, from collapsing. In this way sufficient stiffness is assured so that the entire instrument consisting of the sheath 10 with the obturator 50 in place (FIGS. 1 and 2) within the lumen 18 can be inserted without difficulty through a body opening such as the urethra 44 without buckling, a problem sometimes referred to as a "wet noodle" effect wherein the article being inserted buckles as axial pressure is applied from its outer end during the insertion process. Typically, the obturator 50 has an internal diameter of about 4 mm and the beads can have a diameter of about 2 mm. The obturator 50 is typically formed from a plastic resin such as a polyolefin, e.g polyethylene plastic. A head 54 has an extension 54a cemented inside the free end of the interior 60 of the obturator 50. Similarly, the insertion tip 52 is provided with an axial cylindrical extension 52a which is cemented within the hollow interior 60 of the obturator 50. Following insertion of the instrument into the body, e.g., through the urethra 44, the obturator 50 can be removed. As soon as this is done, the opening 22 at the proximal end of the sheath 10 can be sealed with a removable cap 70 formed from rubber or other suitable material with a central cylindrically-shaped, optionally barbed axial extension 72 that serves as a plug or nipple seal to prevent the loss of fluid from the body.

In another form, the beads 62 are replaced with a fiber-optic bundle 63 (FIG. 2) extending longitudinally the entire length of the obturator 50 and the insertion tip 52 comprises an optical lens for viewing and illuminating a body cavity or passage during insertion of the sheath containing the obturator, as well as after insertion.

Placed transurethrally, the invention permits accessing the entire lower and upper urinary tract by endoscopic instrumentation and offers the operator a spectrum of diagnostic or therapeutic options on preferred procedures. When placed percutaneously or through other body orifices, e.g., the trachea, esophagus or rectum, into other body cavities, it offers the same options. It allows multiple interchange of endoscopic instruments, catheters, drains, etc.

Figure 4:
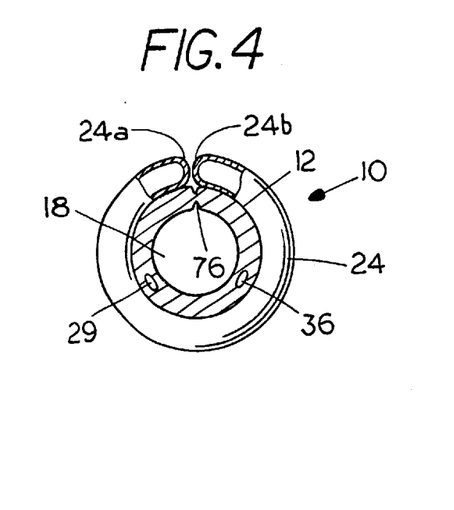
FIG. 4 is a vertical cross-sectional view taken on line 4—4 of FIG. 2A.
Figure 5:
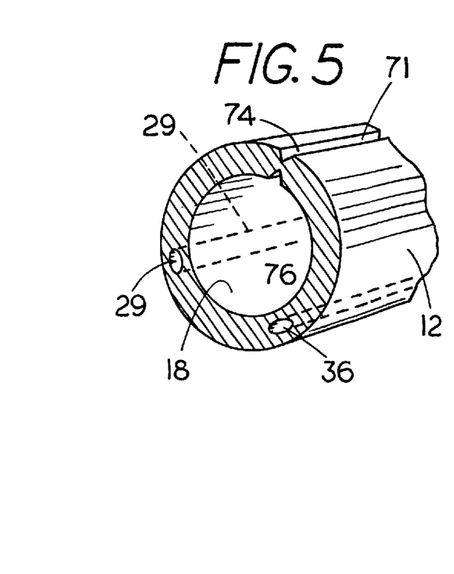
FIG. 5 is a partial perspective view on a larger scale showing a portion of the instrument in accordance with the invention.
Figure 9:
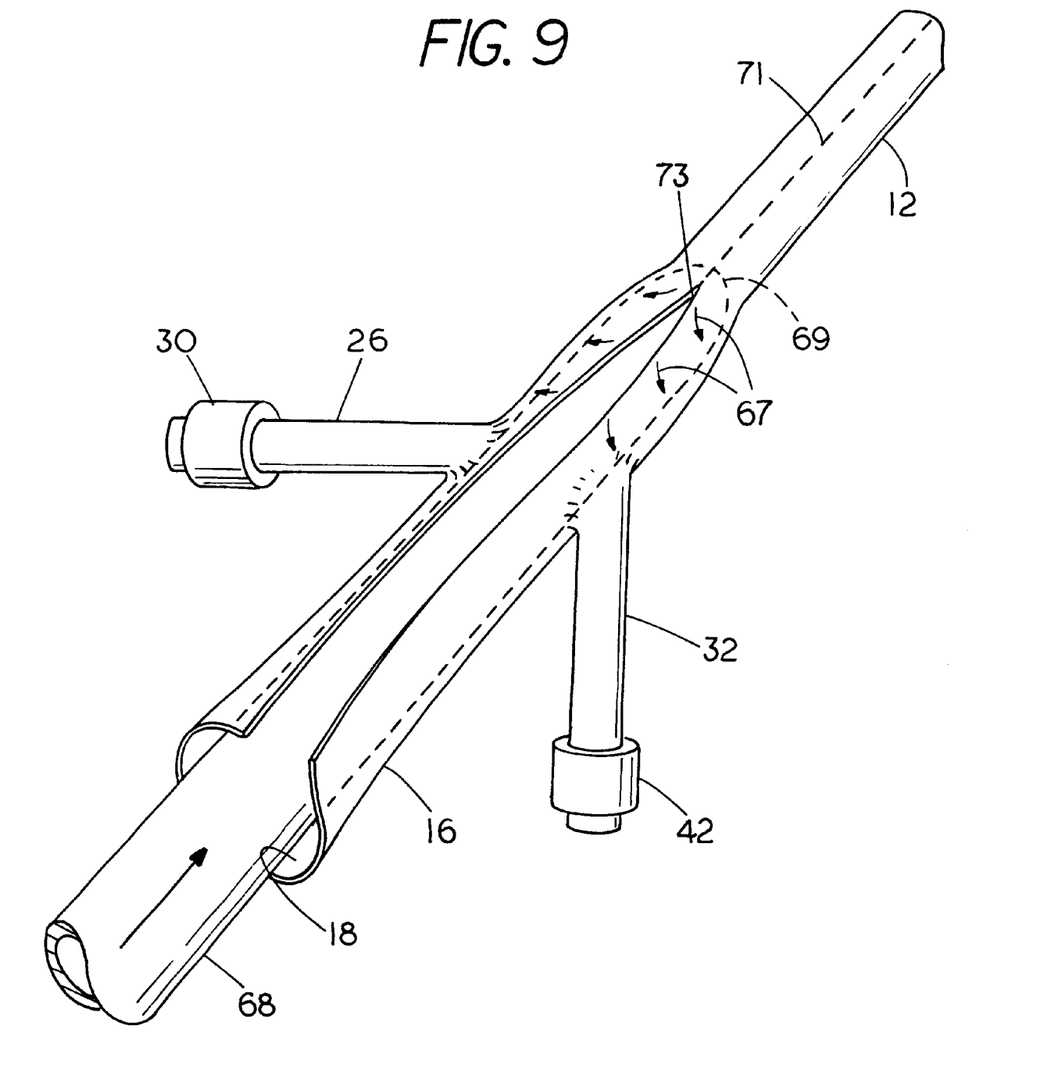
FIG. 9 is a partial perspective view of an optional form of the instrument that is adapted to split open along a separation line during use.

Under certain circumstances it may be necessary to insert a surgical instrument, e.g. 68 as shown in FIG. 9, of a larger diameter than can be accommodated by the lumen 18 of the sheath 10. The present invention provides a feature that facilitates the insertion of such an instrument. Refer now to FIGS. 4, 5 and 9. As shown in these figures, the sheath 10 is provided with a longitudinally extending line of weakness which serves as a separation line 71 along which the sheath 10 can split open as shown at 73 (FIG. 9). Thus, when the oversized instrument 68 is inserted, the pressure produced by the tip 69 of the instrument 68 will be directed circumferentially as indicated by the arrows 67 of FIG. 9. This stress will then split the wall 12 of sheath 10 open along the separation line 71 progressively proceeding toward the distal end 14 of the sheath 10 as the oversized instrument 68 is moved toward the right in FIG. 9. The separation line 71 can be provided by molding aligned longitudinally extending V-shaped indentations 74 and 76 into the wall 12 of the sheath 10 or, if desired, only a single indentation 76 can be used. Alternatively, when the sheath 10 is formed from an extruded plastic tube having an axial molecular orientation, no indentation 74 or 76 is needed. In that case, a tear can be initiated at a starting notch or slit 77 provided at 73 in the open end 22 (FIG. 2) and, once the ring 48 has been removed, the sheath 10 will continue to split open axially as the oversized instrument 68 is forced into the sheath 10. When the splitting at 73 is initiated, a low coefficient of friction on the two mating surfaces is desirable so that the force is exerted to split the sheath 10 without causing excessive frictional drag. After the entire sheath 10 is split open, the balloon 24 is deflated as the seal with the sheath wall 12 is eliminated. The edges of the sheath 10 where it is split apart are not sharp and therefore will not macerate the lining of the urethra 44 during withdrawal. The unique splitting open or unzip feature provided by the separation line 71 already described, which is preferably situated midway between the extensions 26 and 32, allows placement of an oversized instrument, catheter or other device of greater outside diameter than the lumen 18 of the sheath 10. The unzip feature of the instrument is activated and initiates a splitting of the working sheath 10 as the oversized instrument, drain, catheter or other device 68 is inserted, thus opening the working sheath 10 completely.

Figure 6:
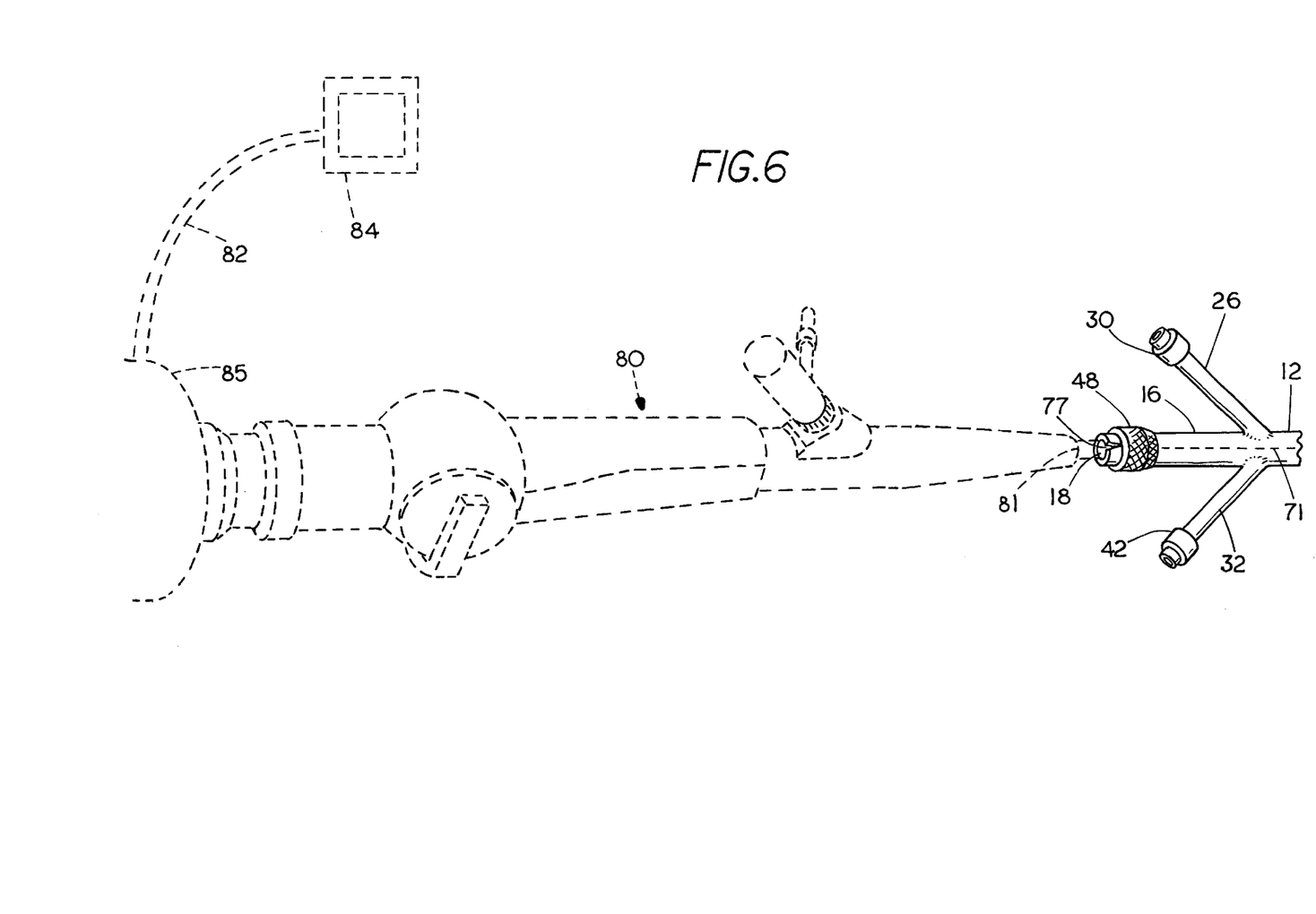
FIG. 6 is a perspective view of the proximal end of the invention showing the insertion of an endoscope through the lumen thereof.
Figures 7, 8:
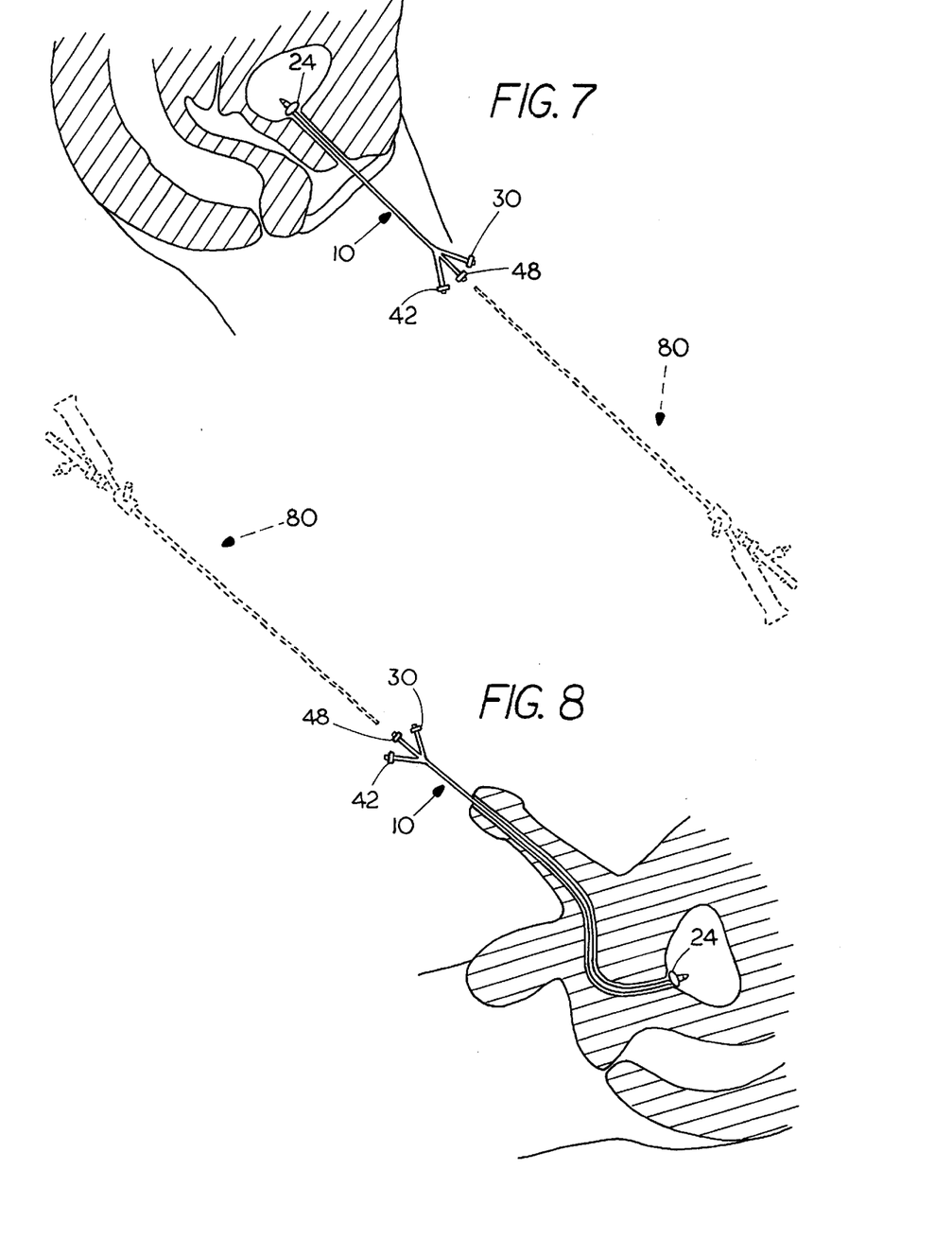
FIG. 7 shows the instrument in place within the female urethra.
FIG. 8 shows the instrument positioned in the male urethra.

Refer now to FIG. 6 which illustrates how the working sheath 10, after placement in the uriniary tract via the urethra, male or female as the case may be, facilitates the insertion of an endoscopic or fiber-optic instrument 80 of known commercially available construction with an optic linkage 82 via camera 85 to a light source 84 for projection to make possible the inspection and visible exploration of the entire urinary tract or other body cavity via percutaneous entry. If desired, the obturator 50 containing the fiber-optic bundle 63 (FIG. 2) can be optically connected at its proximal end with the distal end 81 of the fiber-optic instrument 80 of FIG. 6 so that illumination and viewing of a body passage or cavity can be carried out through the obturator 50.

The invention has numerous benefits and advantages. It offers a passive assistance to the operating physician. For example, in urology during endoscopic procedures, placement in the urethra provides additional patient safety, reduced tissue trauma, increased comfort and speed during the procedure with minimal tissue irritation. It thus potentially reduces healing time, along with iatrogenic infection. Moreover, the instrument of the present invention can be made disposable, as well as being readily placed and retained in the male or female urethra during use and is subsequently easily removed upon procedure completion for discard when in a disposable form. The instrument can be fabricated from any suitable biocompatible, polymeric material in compliance with CDRH as well as FDA standards and specifications. It can be easily mastered for efficient use, as minimal training would be indicated.

The obturator 50 can be employed as described hereinabove or, if desired, the obturator 50 can comprise a commercially available endoscope of suitable known construction which will then serve as an obturator during placement of the working sheath 10 in the urethra or other body or surgical opening in the body. The invention can also be used to access gastrointestinal or pulmonary tracts or percutaneously into any body cavity.

The invention provides numerous endoscopic instrument choices: cystoscope, ureteroscope, future specialized urological endoscopes, electro-cautery delivery, light and laser light delivery, and the like. The obturator 50 can be configured for conformation to male or female urethra multiple angulations, i. e., can be curved as desired. In addition, the invention is applicable in multiple medical specialties including urology, gynecology, general surgery, vascular surgery, gastroenterology and pulmonary medicine, radiation treatment, etc. Since the invention provides a large working sheath for lavage capability or instrumentation in the sheath 10 itself, the fiber-optics that are inserted through the lumen 18 offer better visualization to the operator. The Luer locks 30 and 42 limit instrument position shifting and back flushing. In addition, larger and/or rigid instruments can be easily passed through the working sheath 10 without trauma to the urethral tissue, thus offering greatly improved patient comfort.

Endoscopic and percutaneous procedures prior to the present invention frequently required time consuming insertion and removal of instrumentation which commonly caused tissue trauma, discomfort and pain as the instrument was passed to the surgical site. General anesthesia was frequently necessary because of the discomfort and pain associated with these procedures. The invention inherently makes many of these issues moot. Also, as a result of the above benefits, the invention reduces the risk of iatrogenic infection, bacteremia and/or potential sepsis common with the trauma associated with the insertion and removal of multiple instruments endoscopically or percutaneously. Once placed in the urethra, the sheath prevents scarring and maceration of urethral tissue when multiple procedures and instruments are passed. This saves a substantial amount of time for the physician and reduces patient discomfort or pain. The invention can be adapted to access the upper urinary tract for efficient diagnosis, identification and manipulation of bladder and kidney stones of various types with minimal discomfort to the patient. Bladder stones and other foreign objects can be rapidly removed without tearing the urethral mucosa. The invention also facilitates more office or outpatient surgery as it minimizes the need for general anesthesia.

The invention is also useful in laparoscopic bladder suspension procedures so that the operator can identify the bladder wall for suture or staple placement. The cystoscope operator can direct light on the internal bladder wall and extract a staple or suture through the urethral exit route using the invention. Moreover, the invention has a channel 36 built in that can be used with a negative pressure for aspiration of laser or Bovi smoke or vapor through a filter and trap system external to the urethra. The negative pressure port 36 for laser smoke or vapor removal passes into a filter trap disposal system (not shown).

The invention also facilitates the withdrawal of debris such as bladder or kidney stones which can be removed in larger fragments or by irrigation after being crushed mechanically or by lithotriphy (sonically, laser or electrohydraulic energy), either by aspiration through the lumen 18 or through a catheter (not shown) that is placed within the lumen 18. In this way debris can be removed without anesthesia or pain and with minimal tissue trauma using a rubber catheter (not shown) placed within the sheath 10. Less postoperative pain, faster healing, discharge of medication and endothelial cells or urme is assured.

Briefly, in removing kidney stones, the procedure is commenced with the working sheath 10 in place in the urethra. If desired, the unzip option is invoked to place a larger diameter catheter 68 within the sheath 10. Ureteroscopy can be done with a ureteroscope which can be rigid or flexible through the working sheath 10 surrounding the instrument substantially reduces patient discomfort and length of the procedure.

The instrument according to the invention is delivered to the physician in a sealed package (not shown) with the obturator 50 in place within the lumen 18 of the working sheath 10. At this point the obturator 50 can be removed and replaced with a cystoscope or other suitable instrument that serves as an obturator for insertion if the operator so chooses. Insertion, either by the obturator 50 or the cystoscope 80 is made until the inflation balloon 24 clears the opening of the bladder 46. This can be determined by reading the depth of the insertion lines (not shown) that are printed on the sheath 10 at the urethral entry point. A lubricant and anesthetic gel or fluid should be employed in the urethra to facilitate placement with minimum pain. Upon inflation of the balloon 24 through the duct 29 with gas or fluid, a slight retracting pull should be made to assure that the bladder wall has retained the sheath 10. The check valve in the Luer lock 30 will maintain the pressure to keep the balloon 24 inflated. The obturator 50 then can be withdrawn and a cystoscope 80 placed within the sheath 10 to view the inside of the bladder 46. This is accomplished by grasping the proximal end 16 of the sheath 10 with the left forefinger and thumb by means of the grasp ring 48 and retracting the obturator 50 with the other hand. The obturator 50 will have served its role to insert the sheath 10 through the many curves of the urethra 44 into the bladder 46. The working sheath 10 is now in place so as to permit therapeutic treatment or diagnostic perspective for the operator. The instillation ducts 34, 36 can deliver solutions, e.g., lidocaine for numbing the tissue, medication, etc., and an endoscopic device 80 can be introduced to deliver light e.g., laser energy for viewing or desired treatment (sulgaratic, cryonic, pyronic, electro-cautery, Bovi) and the like.

During laparoscopic surgery, in the space of Ritzius (the preperitoneal cavity), it can be to the patient's and surgeon's advantage (with respect to visual positive identification orientation minimization of urinary tract infections and contamination, the time required for reinsertion of a cystoscope, etc.) to have rapid access to an internal view of the bladder itself, and this is readily accomplished through the use of the present invention. Staple and suture penetration of the bladder wall is visually apparent and a urethral catheter or stent can be inserted through the sheath 10. The light provided by an endoscope can be used to transilluminate and delineate the bladder or bladder wall during: laparoscopy. Enlargements,.wall thickening, vessel enrichment, which all may herald benign or malignant growth, should be more apparent to the operator using the invention. The invention also facilitates the disposal of urine from the bladder that is generated during the procedure. One primary advantage of the invention is to permit rapid insertion and removal of the cystoscope 80 or other useful instrument during endoscopic operative procedures while minimizing the time required to complete the operation while reducing crosscontamination and infection generation, all of which are very advantageous to the patient by ensuring safety while minimizing the time during which the patient is at risk.

EXAMPLES

Typical methods of using the instrument in accordance with the invention will now be described by way of example.

Example 1

The use of the instrument in accordance with the present invention will be described in carrying out a transurethral resection of a bladder tumor. This procedure is usually performed under a general or spinal anesthetic because of the discomfort/pain from passage of the instrument and also from that which might occur from the resection of the tumor by electrical current. However, if one is using laser energy (neodinium YAG or Holmium lasers, for example),.the patient's intraoperative discomfort/pain is usually less as these procedures can, in that case, be performed without general or spinal anesthesia.

First, the working sheath 10 is inserted through the urethra as shown in FIG. 2. The obturator 50 is then removed. Generally, a rigid cystoscope (usually 20–23 French) is passed through the lumen 18 of the sheath 10 with a rigid optical lens to evaluate the urethra and bladder to determine the number of tumors, their locations, extent of involvement of the bladder, and possible involvement of ureteral orifices (where the ureters enter into the bladder). After the endoscopic assessment is performed with the rigid scope, it is removed and the biopsy instrument can be passed through the lumen 18 of the instrument 10 to obtain small biopsies of the tumor and other locations in the bladder. At this point, to treat the tumors by resection (usually electrocautery), the entire rigid cystoscope and scope is removed from the lumen 18 while the instrument 10 remains in place so that a larger instrument (resectoscope) can be passed through the lumen 18. It is not uncommon that, prior to the passage of this larger instrument, it will be necessary to dilate the urethra with a series of instruments called 'sounds' to at least 28 French or larger depending on the size of the resectoscope chosen (and this is based generally on the size of the tumor to be resected).

The resectoscope is passed through the lumen 18 of the sheath 10, either blindly with its own obturator in place therein or under direct vision with a rigid fiber-optic scope in place. The resection of the tumor or tumors is then undertaken. Eventually, the tumor fragments will have to be removed. The tumor fragments may be removed during the procedure if necessary, or at the end of the procedure.

Once a satisfactory resection and removal of tumor fragments has been accomplished, it is necessary to remove the rigid resectoscope from the lumen 18 and pass a catheter through the lumen 18 for temporary irrigation and drainage of the bladder or leave the sheath 10 in place and hook up to a drainage bag for irrigation. Continuous postoperative irrigation may be necessary, as inevitably there will be bleeding after the procedure. If the blood is not irrigated out, clots will form which will result in obstruction of the catheter or, if the catheter has not been left in the urethra, resulting in urinary retention. On occasion, bleeding can be so extensive that clot formation cannot be prevented despite irrigation. In these situations, the patient is usually taken back to the operating room on an emergent basis and given another general anesthetic so the patient will not experience severe pain upon reinsertion of instrumentation such as a resectoscope.

Some of the primary advantages of the invention are the following. First, depending on the size of the tumor, the entire procedure may be accomplished under local anesthetic and limited sedation because manipulation of the lower urinary tract would be limited to the initial passage of the working sheath 10. This would be quite similar to the office cystoscopy which requires generally only topical anesthesia (lidocaine jelly instilled into the urethra). Second, tissue trauma or injury which can cause bleeding or scarring is minimized because there would be no repeated trauma to the urethral mucosa lining. Third, if it is necessary to pass a larger catheter for irrigation and drainage at the end of the procedure, this can be done without significant discomfort or trauma because of the unzip feature of the sheath 10 which allows it to. Split at 73 along line 71. Fourth, postoperative bleeding, which may necessitate a return to the operating room, may be handled on the floor or, if necessary, in the operating room without an anesthetic, as an armamentarium of available endoscopic instruments could be passed through this working sheath 10. Fifth, the overall procedure should be less time consuming because of the rapidity with which instrumentation can be passed through the working sheath 10. This assures safe passage of instrumentation to the operative site (bladder) and reduced risk of false passage into the urethra which can occur upon multiple passage of instrumentation transurethrally. Finally, economic savings can be realized because of less time in the operating room, less or lack of anesthesia, surgeon's time, and disposable instrumentation.

Example 2

The invention will now be described in conducting a laparoscopic pelvic reconstruction procedure, e.g., culposuspension, paravaginal repairs, and enterocele repairs.

First, the working sheath 10 is inserted as shown in FIG. 2. The obturator 50 is then removed. A Foley catheter is then passed through the lumen 18 of the sheath 10 to keep the bladder empty, or the sheath 10 itself can be used for this purpose without a Foley. When the procedure is performed laparoscopically through the working sheath 10, it is frequently necessary to perform a cystoscopic evaluation with the examination of the bladder by passing urethral catheters through the lumen 18 (performed cystoscopically) during or at the end of the laparoscopic procedure. The Foley catheter is removed and the cystoscope is introduced next through the lumen 18 of the sheath 10.

If it is necessary to perform the evaluation during the laparoscopic procedure, it is necessary that the surgeon carry out the procedure from the operative site on the abdomen to between the patient's legs and remove a Foley catheter that was placed in the sheath 10 at the beginning of the procedure to keep the bladder empty, therefore minimizing injury rate during the laparoscopic exposure and dissection necessary to perform the above reconstructive procedures. After the Foley has been removed, the surgeon must then pass a rigid cystoscope through the lumen 18 of the sheath 10 to inspect the bladder or to pass ureteral catheters.

The advantages are many if one is able to use the working sheath 10. First, transurethral diagnostic and endoscopic procedures are performed without having to remove the sheath 10 which was placed at the beginning of the procedure for bladder drainage. This by itself would decrease intraoperative time. Second, having the surgeon leave the intra-abdominal operative site to take a position below is avoided. He can simply pass the flexible scope through the lumen 18 of the working sheath 10 to inspect the bladder and possibly even define the bladder transurethrally which is frequently helpful when performing a laparoscopic procedure. Third, even ureteral catheterization could be performed. Actually, the working sheath 10 gives the surgeon the option of not even having to place the patient in the dorsal lithotomy position for these procedures if a flexible scope or instrumentation is used. The procedure described also potentially decreases the risk of intraoperative iatrogenic infections.

Example 3

The invention will be described in removing kidney stones.

Nephrolithiasis (renal and ureteral calculi) are quite common urologic problems, requiring emergent surgical intervention. When renal or ureteral calculi are causing blockage of the upper urinary tracts, patients will most commonly experience severe and disabling colicky pain requiring immediate emergency medical attention, including pain management and surgical intervention. No population is immune from the renal colic attack as a result of kidney stones (and as will be discussed later), especially astronauts who are at even greater risk. When these attacks occur, patients are initially evaluated in the emergency room. Once the diagnosis of Nephrolithiasis is made, they are admitted to the hospital for management and probable surgical intervention if it is unlikely they will pass the stone on their own or if pain management is a problem.

First, the working sheath 10 is introduced into the bladder as shown in FIG. 2 and the obturator 50 is then removed. The surgical procedure will depend on the size and location of the stone along with complicating factors. If the stone is in the upper urinary tract (kidney or upper two-thirds ureter), it is possible to disintegrate the calculus by extra-corporeal shock wave lithotriphy. However, if the stone is causing high grade obstruction of the ureter, it will be necessary to pass a ureteral stent through the lumen 18 of the instrument 10 to relieve the obstruction and also alleviate the pain. The stent is generally passed transurethrally through the lumen 18 after the patient has received a general anesthetic. This is accomplished by placing the patient in the dorsal-lithotomy position. A rigid cystoscope is then passed transurethrally through the sheath 10 into the bladder. Through the scope, the stent is then negotiated into the ureteral orifice and into the upper collecting system, bypassing the calculus.

Generally, the stent is positioned in the upper collecting system using fluoroscopic guidance. Fluoroscopy may not be necessary if one has an accurate pre-operative measurement of the ureter, which can be obtained from an excretory urogram. Sometimes, the surgeon may elect to extract the calculus rather than passing a stent, and this is done by removing the cystoscope and then inserting a ureteroscope. The ureteroscope is then negotiated through the ureteral orifice up into the ureter to the point where the calculus is visualized. A stone basket is passed through the operating channel of the ureteroscope and the calculus is extracted under ureteroscopic guidance. Because of the edema and inflammation from the calculus itself and manipulation of the calculus, the. ureter will frequently obstruct and this will cause further pain to the patient. The most common way of addressing this problem is to place a ureteral stent after the calculus ahs been extracted.

The advantages of the working sheath 10 of the present invention are obvious. They include a possibility of performing this procedure without a general anesthetic, less operative time, and less chance for infection.

The invention can be used in treating a condition that is experienced by astronauts. The most common surgical emergency that has plagued astronauts has been the formation of Nephrolithiasis as a result of being in a weightless environment. The weightless environment is quite similar to what is experienced by patients who are immobilized. Astronauts and patients who are immobilized experience calcium mobilization and subsequent increased urinary excretion, which can result in the formation of renal calculi. When astronauts experience renal colic, this is truly a grave situation as they are unable to perform their duties. With the increasing distance and duration of space missions and NASA's plans to man a space station in the next 30 years, it will be impossible to return astronauts to earth for medical treatment and since space navigation tends to lead to unbearable renal colic pain, the strongest parenteral pain medication is required. These patients also experience severe nausea accompanying the pain. NASA is presently trying to come up with solutions to treat these episodes in space. One of the greatest challenges is to give a general anesthetic in space as it requires someone skilled in giving anesthesia and because administering anesthesia and I.V. fluids in space is a very challenging problem requiring specialized equipment and techniques. An important advantage of the present invention in this application is the potential for allowing treatment of these stones endoscopically without a general anesthetic.

Many variations are possible. For example, a void valve (not shown) can be provided at the proximal end of the lumen 18 for controlling urine flow from the bladder 46 into a disposable bag.

Many variations of the present invention within the scope of the appended claims will be apparent to those skilled in the art once the principles described herein are understood.

What is claimed is:

1. A method for facilitating endoscopic examination or surgical procedure performed on a patient, said method comprising:

providing a multiple use working sheath having an elongated tubular body with a central longitudinal lumen of sufficient size to accommodate elongated surgical or viewing devices that are to be inserted through the lumen of the sheath into the body of patient, said lumen having an opening at a proximal and distal end thereof, providing the sheath with at least one longitudinally extending separation line defined by a longitudinal weakness therein that facilitates progressive splitting open of the sheath when a device that is larger than the internal diameter of the sheath is passed through the lumen thereof, placing said sheath within the body of the patient, allowing the sheath to remain in contact with the body of the patient until the examination or surgery is complete, inserting and removing one or more surgical devices that are larger than the lumen of the working sheath to cause the sheath to split open progressively along a separation line from pressure provided by a tip of the device as the device is inserted therein, conducting said examination or procedure while the split-open sheath remains in place for enabling the sheath to serve as an artificial protective liner in the body of the patient through which it is passed to minimize tissue trauma while reducing discomfort and pain during the procedure, and thereafter removing the sheath from the body.

2. The method of claim 1 including, providing said sheath with a pair of peripheral longitudinally extending ducts in which one such duct communicates with an inflatable circumferentially extending retention balloon at the distal end of the sheath, and the other of said peripheral ducts communicates with an outlet opening positioned proximate to and proximal of the retention balloon for introducing anesthetic, medications and the like into the body of the patient.

3. The method of claims 2 including, providing the proximal end of each of said peripheral ducts with a check valve at a proximal end thereof.

4. The method of claim 1 including, providing a grasp member having a high friction external surface thereon at a proximal end of said working sheath and manipulating the sheath during use by means of the grasp member.

5. The method of claim 1 including, providing a removable obturator within the lumen of the sheath comprising a tube formed from a collapsible material having a plurality of support members positioned therein to prevent the obturator from collapsing when external pressure is applied to the wall of the obturator and the obturator is closed at each end thereof.

6. The method of claim 1 wherein the sheath is introduced transurethrally into the body of the patient.

* * * * *